United States Patent [19]

Nordgren et al.

[11] 3,995,622
[45] Dec. 7, 1976

[54] DEVICE FOR DETERMINING CHANGED PULSES

[75] Inventors: Lars Carl Ernst Nordgren; Christer Ivar Malmstroem, both of Uppsala, Sweden

[73] Assignee: Siemens Aktiengesellschaft, Munich, Germany

[22] Filed: Apr. 25, 1975

[21] Appl. No.: 571,718

Related U.S. Application Data

[63] Continuation of Ser. No. 126,660, March 24, 1971, abandoned.

[52] U.S. Cl. .......................................... 128/2.06 A
[51] Int. Cl.² ........................................... A61B 5/04
[58] Field of Search ............... 128/2.05 R, 2.05 S, 128/2.06 A, 2.06 B, 2.06 F, 2.06 R, 2.1 B, 2.1 R

[56] References Cited
UNITED STATES PATENTS

| | | | |
|---|---|---|---|
| 3,498,288 | 3/1970 | Mat et al. | 128/2.06 B |
| 3,533,402 | 10/1970 | Siedband | 128/2.06 A |
| 3,552,386 | 1/1971 | Horth | 128/2.06 A |
| 3,828,768 | 8/1974 | Douglas | 128/2.06 A |
| 3,903,874 | 9/1975 | Shakgspgre | 128/2.06 A |
| 3,927,663 | 12/1975 | Russell et al. | 128/2.06 A |

Primary Examiner—William E. Kamm
Attorney, Agent, or Firm—Richards & Geier

[57] ABSTRACT

A device is used for determining pulses changed as to form of a pulse sequence, particularly width-widened extra systoles in an electro-cardiogram. The device is particularly characterized by a filter arrangement for separating out frequency parts characterisitic for the form and time properties of pulse sequences from the energy frequence spectrum of the sequence. The device also includes means for evaluating the obtained frequency parts to provide pulse identification.

12 Claims, 6 Drawing Figures

DEVICE FOR DETERMINING CHANGED PULSES

This application is a continuation of an application Ser. No. 126,660, filed Mar. 24, 1971, and now abandoned.

This invention relates to a device for determining pulses changed as to form of a pulse sequence, particularly width-widened extra systoles in an electro-cardiogram.

Devices of this type constitute valuable auxiliary means in conjunction with diagnosing, treating and supervising various heart diseases, such as infarcts. Known devices operate according to several very different methods.

According to one of such methods the amplitude of a QRS complex of an EKG pulse sequence is measured and possibly also the time is determined during which a measured amplitude exceeds a given amplitude limit. In this method it is assumed that the obtained QRS complexes have larger amplitudes than the normal ones. Since this is not always the case this measuring method is comparatively unsafe.

According to another method the QS-duration is determined. The measuring safety of this method depends on the precision with which the individual zero point values can be measured. Since the zero line of an electro-cardiogram swings to a comparatively large extent it is rather difficult to always find the correct zero points. The finding of the searched for zero passages is also made difficult by the fact that an electro-cardiogram has a large number of zero passages which are of no interest for the actual measuring.

According to a third method the area is determined which is enclosed by a QRS complex. This method assumes that a area enclosed by curves of an exceeded QRS complex is always greater than that of a normal QRS complex. However, there are often QRS complexes which do not have this property.

According to two other methods the amplitude of the QRS complexes is always determined and in addition either the QS time period or the area enclosed by the QRS complexes. Such combination methods, as compared to partial methods, have the drawback that the technical expenditure is correspondingly great and errors in measuring take place quite often.

Finally a method is also known where the R—R interval is subdivided into a plurality of individual time segments and a permissible amplitude value is determined for each time segment. The division of the interval can then be adapted to a slow change of the average value of the heart frequency. Devices operating according to this method also produce unsatisfactory measured results, since the form criterion used for each time segment is merely chosen.

An object of the present invention is to provide a device of the above-described type which will not have the drawbacks of prior art devices and which will provide a precise identification of form-changed pulses, particularly for width-enlarged extra systoles.

Other objects of the present invention will become apparent in the course of the following specification.

In the accomplishment of the objectives of the present invention it was found desirable to provide a filter device for sieving those frequency parts of the pulse sequence out of the energy frequency spectrum which are characteristic for the form and time properties, as well as means evaluating the obtained frequency parts as pulse identification.

The present invention is based on the recognition that form-changed pulses of a pulse sequence have a different energy frequency spectrum than the normal impulses of the same sequence. For example, the high frequencies part of width-extended extra systoles in an electro-cardiogram is much smaller than in the case of normal QRS complexes. By a corresponding evaluation of, for example, high and low frequency parts of the pulse sequence it is then possible to determine whether there are width-extended extra systoles or only normal QRS complexes.

A correspondingly programmed computer can be used as the filter device. From the point of view of switch technology it is simpler, however, to use as the filter device two separate band pass filters tuned to separate frequencies. The average frequencies of the band pass filters should lie preferably between 5 and 35 HZ. It was found that for evaluation purposes such frequencies provide, on the one hand, the best possible evaluation of the energy frequency spectrum and, on the other hand, disturbances caused by the measuring are at a minimum.

The pulse identifying evaluation of frequency parts of a pulse sequence received at the outlet of the filter takes place in a simple manner in that the energy contents of the two impulse sequences at the outlets of the filter are compared with each other and that a signal, for example an alarm, is produced when the energy difference exceeds a predetermined end value. An analog calculator is connected behind the filter device for evaluating and comparing the energy contents which always produces the difference between amplitude squares of the filter outlet signals. The signal which is thus produced is transmitted to a summing device, or example, a pit pass, for a continuing summation of this signal during a time period which preferably corrresponds to the duration of a normal pulse. A discriminator is connected behind the summing device and is actuated when the energy difference exceeds a predetermined end value.

It is advisable to connect a balance amplifier in front of a filter for balancing the different damping of the pulse sequence in the filters. The balance amplifier should be adjustable with respect to an average pulse type, whereby the adjustment can take place, as desired, manually by a resistance potentiometer or automatically depending upon the outgoing signals of the filter, for example, by an integration amplifier operated by the outgoing signals.

To make easier the identification of normal and excessive impulses, it is furthermore advantageous to provide a time reference circuit for producing voltage impulses coinciding its time with signals appearing at the inlet of the discriminator. Preferably, an impulse sequence produced at the outlet of one of the filters passes through the time reference circuit. This suppresses in advance disturbing signals which may appear, as well as uninteresting information about the original impulse sequence.

The voltage impulses of the time reference circuit are transmitted along with outgoing signals of the discriminator to two separate logic combination members, in such manner that one member produces an outgoing signal only when a voltage impulse and a discriminator outgoing signal appear simultaneously, while the other member produces an outgoing signal only when a voltage impulse appears solely from the time reference circuit.

The invention will appear more clearly from the following detailed description when taken in connection with the accompanying drawings showing by way of example only, a preferred embodiment of the inventive idea.

Figure 1:
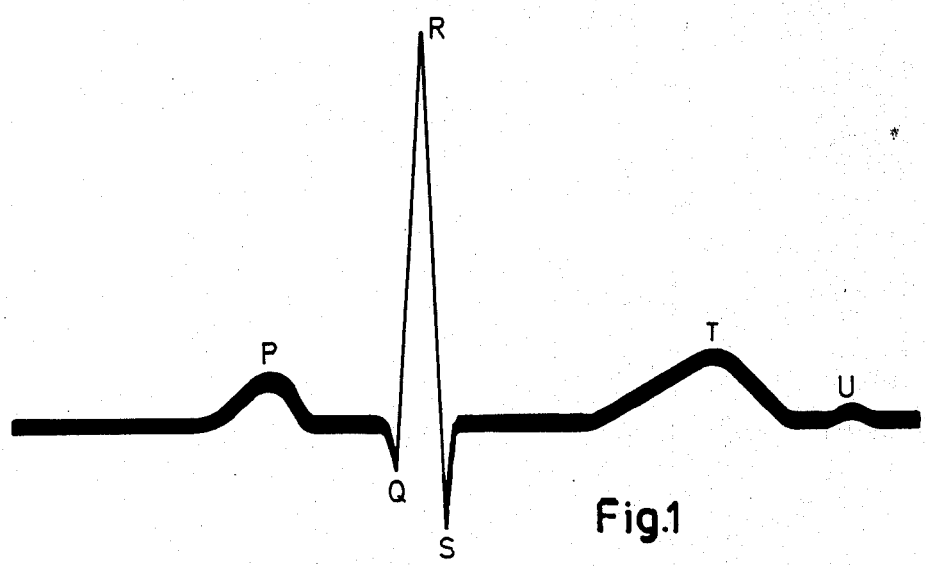
FIG. 1 is a diagram illustrating a normal EKG complex.

The normal EKG complex shown in FIG. 1 can be divided into three parts, namely, a first part relating to the prechamber activity of the heart, which produces the wave P of FIG. 1, a second part representing the main chamber activity and indicated as the wave QRS, as well as the third part which is the rest period of the main chamber and which is indicated by the illustrated wave T. During a diagnostic examination of EKG general criteria are used concerning the shape and amplitide of EKG complexes and the duration of different waves occurring in the complex.

Figure 2:
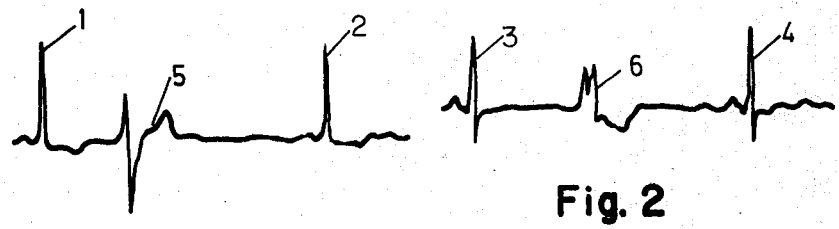
FIG. 2 is a diagram illustrating two different sections of an EKG.

FIG. 2 shows two sections of an EKG. The two sections have normal complexes 1, 2, 3 and 4, as well as overedged (widened) complexes 5 and 6.

Figure 3:
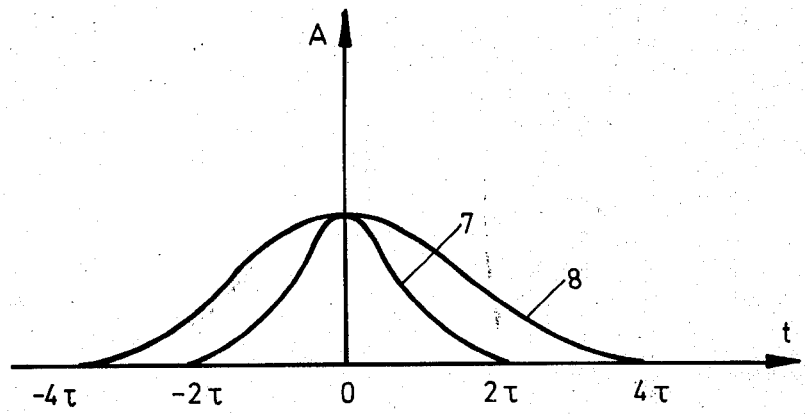
FIG. 3 is a diagram illustrating the movement in time of the amplitude of EKG complexes.

FIG. 3 shows two mathematical samples of the extent of the amplitude of QRS complexes depending on the time $t$. The curve 7 shows approximately a normal QRS complex, while the curve 8 shows approximately a widened QRS complex.

Figure 4:
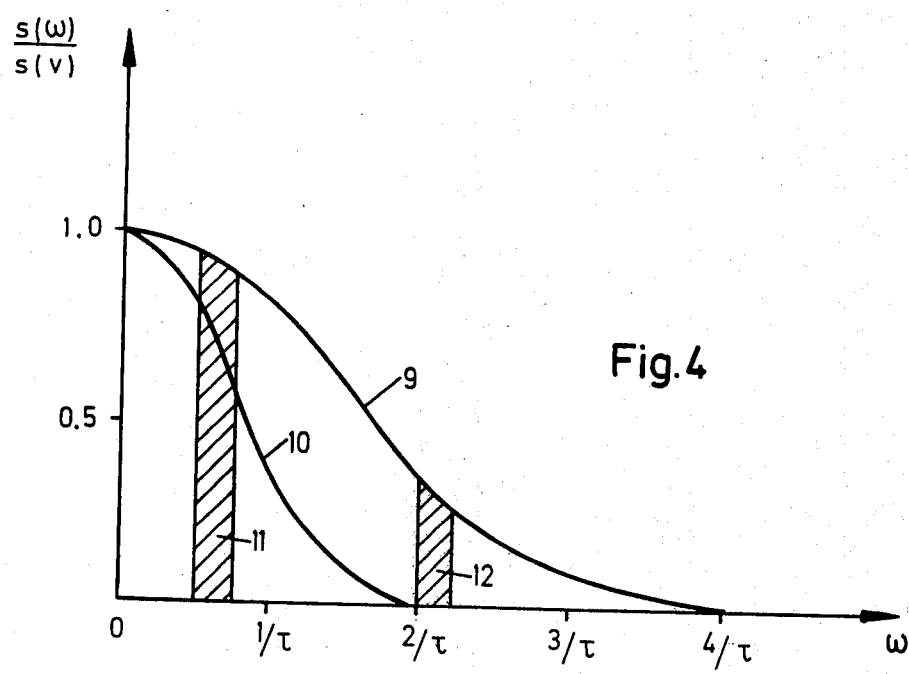
FIG. 4 is a diagram showing spectral frequency divisions.

FIG. 4 shows the spectral frequency distributions of the curves 7 and 8 of FIG. 3. The spectrum of the curve 7 is represented by the curve 9 and the spectrum of the curve 8 by the curve 10. It is apparent that the spectrums of the two curves 7 and 8 of FIG. 3 have substantial differences. These differences can be used as a criterium for the identification of excessive impulses. If, for example, two frequency bands 11 and 12 of FIG. 4 selected from the spectrum curves 9 and 10, are sieved out by two correspondingly set filters and if thereupon the energy difference between the two bands is provided, then the energy difference will be comparatively small when only normal QRS complexes are present; they will be comparatively large, however, in case of excessive complexes. By balancing the different damping of the impulse sequence in the filters it is even possible to attain that the energy difference will be zero in the case of normal QRS complexes, so that a difference in energy will take place only in case of excessive QRS complexes. The difference in energy which then takes place can be measured. If it exceeds a predetermined end value, an alarm signal is produced.

Figure 5:
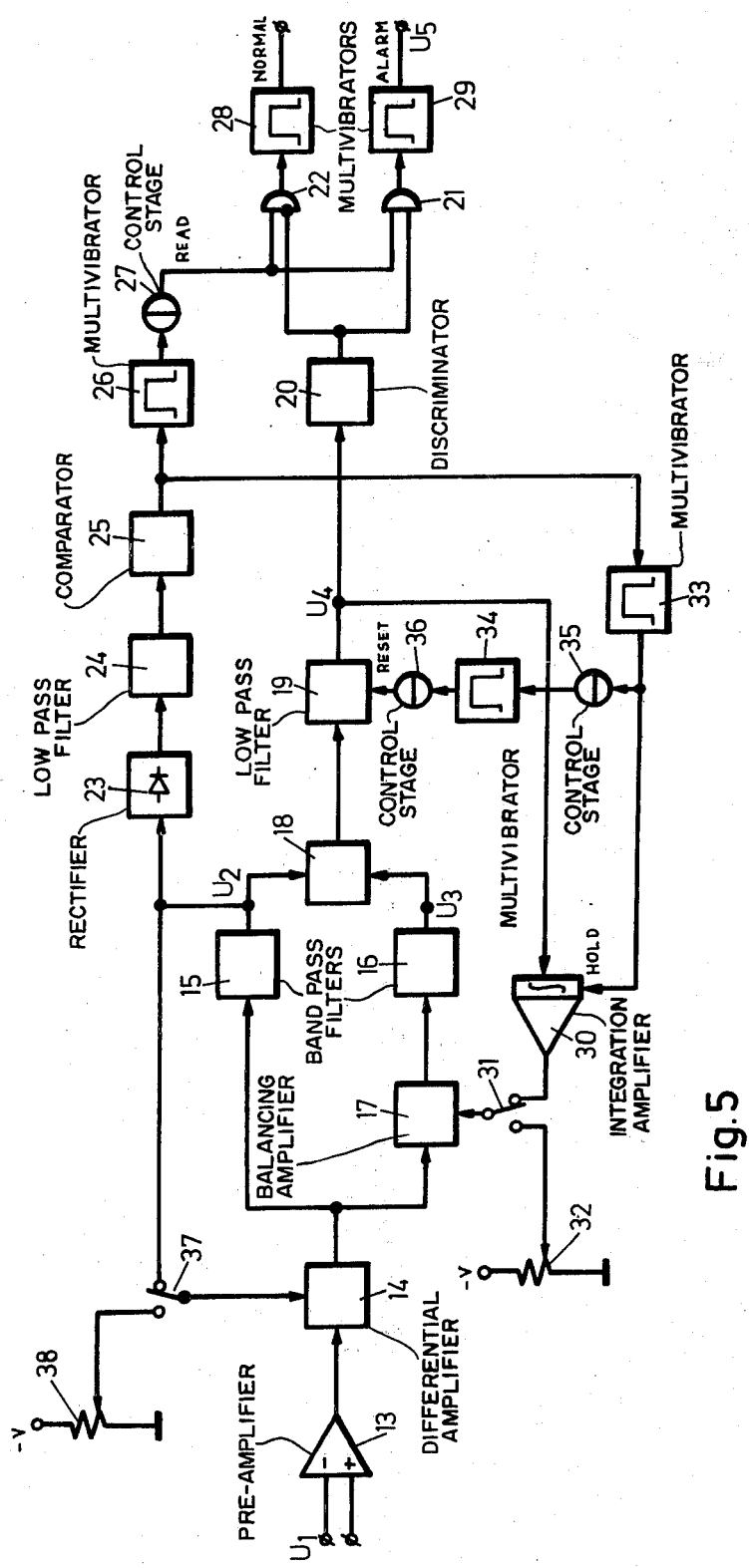
FIG. 5 is a circuit diagram of a device of the present invention.

FIG. 5 shows the basic circuit of a device of the present invention operating in the described manner. According to FIG. 5 an EKG signal $U_1$ obtained by means of EKG electrodes from the body of a patient (not shown) is transmitted to a pre-amplifier 13 (differential amplifier). The amplified signal is adapted in an adaptation amplifier 14 to a measuring unit consisting of a band filter 15, a band pass filter 16 and a balancing amplifier 17 connected ahead of the band pass filter 16.

The band pass filter 15 has a center frequency of about 5 HZ and the band pass filter 16 has center frequency of about 35 HZ. The balancing amplifier 17 is used to balance the different damping of the EKG signal $U_1$ in the two filter branches.

The outgoing signal $U_2$ of the filter 15 which is the low frequency portion of the EKG signal $U_1$ and the outgoing signal $U_3$ of the filter 16 which is the high frequency portion of the EKG signal $U_1$ are supplied to the analog calculator 18 which forms the difference $U_2^2 - U_3^2$ between the amplitude squares of the filter outgoing signals $U_2$ and $U_3$ (two summing stages to form the sums $U_2 + U_3$ and $U_2 - U_3$ and a multiplication stage for the multiplication of the sums). The signal $U_2^2 - U_3^2$ is continuously summed in a low pass filter 19 during a time interval corresponding substantially to the duration of a normal QRS complex. The purpose of the above-described both-sided balancing of the two filter branches, of the provision of the difference between the squares of signals $U_2$ and $U_3$ and of the following summation in the low pass filter 19, is to make zero the energy difference formed in a pulse for a normal QRS complex. If the QRS signal is exceeded, the result is that the signal formed by the low pass filter 19 will be substantially different from zero. If the difference in energy exceeds a predetermined limiting value, the threshold discriminator 20 which is connected behind the low pass filter 19 will be actuated.

The outlet status of the discriminator 20 is felt by two logic combination members 21 and 22 by means of a pulse READ produced in rhythm of the QRS complexes in the original EKG signal $U_1$. If at the appearance of a pulse READ there is a signal at the outlet of the discriminator 20, a monostable-multivibrator 29 connected behind the logic member 21 is excited and produces an alarm. If there is an impulse READ but if the voltage signal at the outlet of the discriminator is zero, then the monostable-multivibrator 28 connected behind the logic member 22 is excited and will indicate the presence of a normal QRS complex. The impulse READ is produced from the outgoing signal $U_2$ of the band pass filter 15 after rectifying in a rectification device 23, filtering in a low pass filter 24, comparision in a comparator 25 and time delay in a monostable-multivibrator 26 with a control stage 27 connected behind it (time reference circuit).

The regulation of the balancing amplifier 17 so as to adapt it to two band pass filter branches can take place automatically depending upon the outlet signal $U_4$ of the low pass filter 19 by an integration amplifier 30. The regulation of the balancing amplifier 17 takes place in such manner that the signal $U_4$ at the outlet of the low pass filter 19 becomes zero when QRS complexes indicative of the patient are produced. The regulation of the balancing amplifier 17 can also take place manually through a resistance potentiometer 32 after the switching of the switch 31.

To prevent the possibility that during the appearance of a pulse the measuring procedure will be disturbed by a change in the balancing of the two filter branches, the integration amplifier 30 is locked at its inlet HOLD during a time period corresponding to the duration of a QRS complex. The locking takes place by the comparator 25 of the time reference circuit. The duration of the locking is fixed by the duration of an impulse produced by a monostable-multivibrator stage 33.

To provide best possible summing properties of the low pass filter 19, it must have a low limit frequency. In order to make certain that a summed QRS wave at high herz frequency will not disturb the following QRS wave, a release circuit is provided for the low pass filter 19 which switches its outlet to a zero potential depending upon the outlet signal of the comparator 25 over monostable-multivibrator 33 and 34, the control stage 35 and 36 and over the control inlet RESET, after the QRS complex (now changed in form) has been summed up. It should be noted that the delay time period of the monostable-multivibrator stage 26 is shorter than the sum of the delay time periods of the monostable-multivibrator 33 and 34. Thus the signal transmitted from the low pass filter 19 to the discriminator 20 can be read before the above-mentioned zero position sets in.

The earlier described adaptation amplifier 14 can be operated selectively automatically from the outlet of the band pass filter 15 (depending upon the signal $U_2$) or manually after switching the switch 37 through a resistance potentiometer 38.

Figure 6:
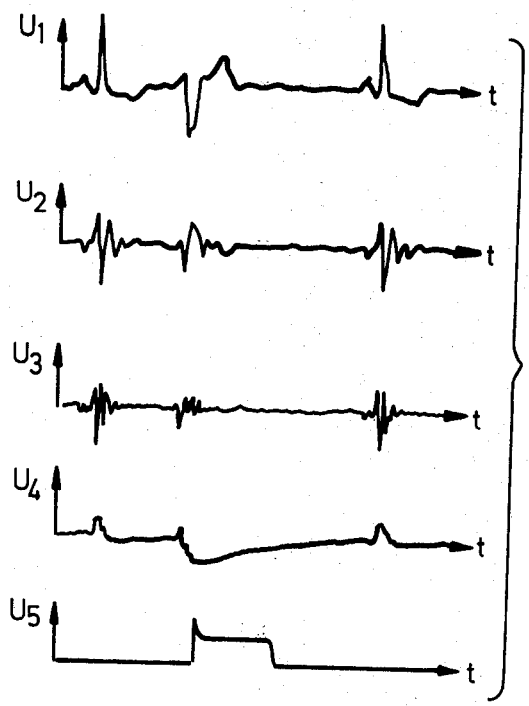
FIG. 6 is a diagram illustrating the voltages appearing in the circuit of FIG. 5.

FIG. 6 shows the time curve of the most important voltages appearing in the circuit diagram of FIG. 5. The voltage $U_1(t)$ corresponds to the EKG signals appearing at the inlet of the preliminary amplifier 13. The voltages $U_2(t)$ and $U_3(t)$ appear at the outlets of the band pass filters 15 and 16. The voltage $U_4(t)$ corresponds to the outgoing signal 1/T
($U_2^2 - U_3^2$) $dt$ of the low pass filter 19. The voltage $U_5(t)$ corresponds to an alarm signal taking place when an excessive QRS complex appears at the outlet of the monostable-multivibrator 29.

The present invention is not limited to the described embodiment but can be changed within the scope of the appended claims.

We claim:

1. A device for detecting pulses changed in form of a pulse sequency, such as widened extra systoles in an electrocardiogram, comprising a filter means or sieving out from the energy frequency spectrum of a pulse sequence frequency portions characteristic for the form and duration of the pulse sequence and means evaluating said frequency portions for pulse identification, wherein said filter means comprises a total of two band pass filters for generating two separate pulse sequences from the original pulse sequence, a first pulse sequence having only such frequencies which are characteristic for both pulses not changed in form and pulses changed in form and a second pulse sequence having only such frequencies which are characteristic for pulses not changed in form and wherein said evaluating means comprise an energy calculator connected to the outputs of the band pass filters, said energy calculator calculating the difference of the energy contents of the separate two pulse sequences, and a threshold discriminator connected to the output of said energy calculator, said discriminator generating a signal when the difference between the energy contents of the two separate pulse sequences exceeds a prefixed value, and an alarming device connected to the output of said discriminator and generating an alarming signal when the discriminator generates an output signal.

2. A device in accordance with claim 1, wherein the band pass filter generating said first pulse sequence is set to a center frequency at 5 Hz and wherein the band pass filter generating said second pulse sequence is set to a center frequency at 35 Hz.

3. A device in accordance with claim 1, comprising balancing means connected to one of said band pass filters for balancing the different damping of the pulse sequence by the filters and further comprising control means operatively connected with said balancing means, said control means controlling said balancing means so that for pulses not changed in form, such as normal QRS-complexes in the electro-cardiogram, said balancing means compensates the damping difference at zero.

4. A device in accordance with claim 3, wherein said balancing means is a balancing amplifier and wherein said control means is a resitance potentiometer having means for manually controlling the gain of said balancing amplifier.

5. A device in accordance with claim 3, wherein said balancing means is a balancing amplifier and wherein said control means is an integration amplifier having means controlling the gain of said balancing amplifier depending upon the outgoing signals of the band pass filters.

6. A device in accordance with claim 1, wherein said energy calculator and said energy comparator consist of an analog calculator calculating the difference between amplitude squares of the outgoing pulse sequences of the band pass filters and a summing up device, such as low pass filter, connected to the output of said analog calculator for summing up the output difference signals of said analog calculator during the duration of pulses in the pulse sequences.

7. A device in accordance with claim 1, comprising a time reference circuit connected with the output of said band pass filter generating the first pulse sequence for producing voltage impulses coinciding in time with signals produced at the inlet of said threshold discriminator, and further comprising two separate logic combination members connected with said time reference circuit and said threshold discriminator and receiving the voltage implses from said time reference circuit along with the outlet signals from said threshold discriminator, one of said members producing an outgoing signal only in case of simultaneous appearance of a voltage impulse of said time reference circuit and a outlet signal from said discriminator and the other one of said members producing an outgoing signal only in case of a sole appearance of a voltage impulse from said time reference circuit.

8. A device in accordance with claim 7, wherein said time reference circuit comprises a rectifying device, a low pass filter connected with said rectifying device, a comparator connected with said filter and a time delay member connected with said comparator.

9. A device in accordance with claim 8, comprising a balancing amplifier for balancing the different damping of the pulse sequence by the band pass filters and an integration amplifier connected with and controlling said balancing amplifier, said integration amplifier being connected to the output of said comparator in the time reference circuit and means for locking said amplifier for the duration of a voltage signal generated at the outlet of said comparator.

10. A device in accordance with claim 8, comprising a release circuit connected with and actuated by said comparator in the time reference circuit for the zero point setting of said summing up device connected to the output of said analog calculator directly after the passage of its outgoing signals to said threshold discriminator.

11. A device in accordance with claim 7, comprising an adaptation amplifier at the original pulse sequence entry and means automatically regulating the gain of said adaptation amplifier depending upon the incoming signals of the time reference circuit.

12. A device in accordance with claim 1, comprising an adaptation amplifier at the original pulse sequence entry and a resistance potentiometer having means for manually regulating the gain of said adaptation amplifier.

* * * * *